United States Patent
Newton et al.

(10) Patent No.: US 7,396,348 B2
(45) Date of Patent: Jul. 8, 2008

(54) MEDICAL VALVE WITH EXPANDABLE MEMBER

(75) Inventors: Brian L. Newton, Woonsocket, RI (US); Andrew L. Cote, Sr., Merrimack, NH (US)

(73) Assignee: Nypro Inc., Clinton, MA (US)

( * ) Notice: Subject to any disclaimer, the term of this patent is extended or adjusted under 35 U.S.C. 154(b) by 713 days.

(21) Appl. No.: 10/224,299

(22) Filed: Aug. 20, 2002

(65) Prior Publication Data

US 2003/0050610 A1    Mar. 13, 2003

Related U.S. Application Data

(60) Provisional application No. 60/314,210, filed on Aug. 22, 2001.

(51) Int. Cl.
*A61M 5/00* (2006.01)

(52) U.S. Cl. .................................... 604/256

(58) Field of Classification Search ......... 604/256–257, 604/246–249, 905, 34, 236–237, 261, 99.04, 604/167.03, 167.04
See application file for complete search history.

(56) References Cited

U.S. PATENT DOCUMENTS

| | | | |
|---|---|---|---|
| 2,594,405 A | 4/1952 | Deters | 137/53 |
| 2,693,801 A | 11/1954 | Foreman | 128/214 |
| 2,705,501 A | 4/1955 | Frizsch et al. | 137/113 |
| 2,756,740 A | 7/1956 | Deane | 128/1 |
| 2,899,975 A | 8/1959 | Fernandez | 137/543.17 |
| 2,999,499 A | 9/1961 | Willett | 128/214 |
| 3,087,492 A | 4/1963 | Garth | 128/350 |
| 3,105,511 A | 10/1963 | Murphy, Jr. | 137/399 |
| 3,192,949 A | 7/1965 | De See | 137/540 |
| 3,385,301 A | 5/1968 | Harautuneian | 128/349 |
| 3,399,677 A | 9/1968 | Gould et al. | 128/349 |
| 3,416,567 A | 12/1968 | Von Dardel et al. | 137/604 |
| 3,506,005 A | 4/1970 | Gilio et al. | 128/214 |

(Continued)

FOREIGN PATENT DOCUMENTS

EP    0268480 A1    5/1988

(Continued)

OTHER PUBLICATIONS

Authorized Officer Henriette Jablanovski, *The International Search Report*, International Searching Authority, Jun. 3, 2003, 9 pages.

*Primary Examiner*—Nicholas D. Lucchesi
*Assistant Examiner*—Theodore J Stigell
(74) *Attorney, Agent, or Firm*—Bromberg & Sunstein LLP

(57) ABSTRACT

A medical valve has a resilient member that is forcibly expanded to an expanded volume from a normal volume. Specifically, the valve operates in a closed mode that prevents fluid flow, and an open mode that permits fluid flow. To these ends, the valve has a housing having an inlet and an outlet, and the noted resilient member within the housing. The resilient member and housing form a fluid channel between the inlet and the outlet. The fluid channel at least in part extends through the resilient member. The fluid channel has a given portion formed by a variable volume portion of the resilient member. The variable volume portion has a normal volume when in the closed mode, and an expanded volume when the open mode. The expanded volume is greater than the normal volume.

29 Claims, 6 Drawing Sheets

U.S. PATENT DOCUMENTS

| | | | |
|---|---|---|---|
| 3,538,950 A | 11/1970 | Porteners | 137/608 |
| 3,570,484 A | 3/1971 | Steer | 128/214 |
| 3,572,375 A | 3/1971 | Rosenberg | 137/512 |
| 3,726,282 A | 4/1973 | Patel | 128/349 BV |
| 3,806,086 A | 4/1974 | Cloyd | 251/149.7 |
| 3,831,629 A | 8/1974 | Mackal et al. | 137/525 |
| 3,838,843 A | 10/1974 | Bernhard | 251/149.1 |
| 3,923,065 A | 12/1975 | Nozick et al. | 128/348 |
| 3,965,910 A | 6/1976 | Fischer | 128/349 R |
| 3,994,293 A | 11/1976 | Ferro | 128/214 R |
| 4,063,555 A | 12/1977 | Ulinder | 128/214 R |
| 4,080,965 A | 3/1978 | Phillips | 128/214 D |
| 4,094,195 A | 6/1978 | Friswell et al. | 73/422 GC |
| 4,094,196 A | 6/1978 | Friswell | 73/422 GC |
| 4,116,201 A | 9/1978 | Shah | 128/351 |
| 4,121,585 A | 10/1978 | Becker, Jr. | 128/214 R |
| 4,143,853 A | 3/1979 | Abramson | 251/149.1 |
| 4,223,808 A | 9/1980 | Williams et al. | 222/88 |
| 4,300,571 A | 11/1981 | Waldbillig | 128/673 |
| 4,324,239 A | 4/1982 | Gordon et al. | 128/214 R |
| 4,333,455 A | 6/1982 | Bodicky | 128/214.4 |
| 4,334,551 A | 6/1982 | Pfister | 137/614.03 |
| 4,344,435 A | 8/1982 | Aubin | 128/350 R |
| 4,387,879 A | 6/1983 | Tauschinski | 251/149.1 |
| 4,401,432 A | 8/1983 | Schwartz | 604/89 |
| 4,421,296 A | 12/1983 | Stephens | 251/149.7 |
| 4,458,480 A | 7/1984 | Irwin | 60/39.63 |
| 4,496,348 A | 1/1985 | Genese et al. | 604/167 |
| 4,498,658 A | 2/1985 | Mikiya | 251/149.6 |
| 4,534,758 A | 8/1985 | Akers et al. | 604/85 |
| 4,535,820 A | 8/1985 | Raines | 137/854 |
| 4,550,785 A | 11/1985 | Hibbard et al. | 173/134 |
| 4,551,136 A | 11/1985 | Mandl | 604/141 |
| 4,585,435 A | 4/1986 | Vaillancourt | 604/27 |
| 4,596,557 A | 6/1986 | Pexa | 604/86 |
| 4,611,973 A | 9/1986 | Birdwell | 417/342 |
| 4,617,015 A | 10/1986 | Foltz | 604/100 |
| 4,661,110 A | 4/1987 | Fortier et al. | 604/256 |
| 4,675,003 A | 6/1987 | Hooven | 604/9 |
| 4,681,132 A | 7/1987 | Lardner | 137/271 |
| 4,683,905 A | 8/1987 | Vigneau et al. | 137/329 |
| 4,683,916 A | 8/1987 | Raines | 137/854 |
| 4,698,061 A | 10/1987 | Makaryk et al. | 604/408 |
| 4,710,168 A | 12/1987 | Schwab et al. | 604/99 |
| 4,712,583 A | 12/1987 | Pelmulder et al. | 137/852 |
| 4,743,235 A | 5/1988 | Waldbillig et al. | 604/250 |
| 4,745,950 A | 5/1988 | Mathieu | 137/798 |
| 4,749,003 A | 6/1988 | Leason | 137/854 |
| 4,752,287 A | 6/1988 | Kurtz et al. | 604/99 |
| 4,752,292 A | 6/1988 | Lopez et al. | 604/244 |
| 4,758,224 A | 7/1988 | Siposs | 604/119 |
| 4,776,369 A | 10/1988 | Lardner et al. | 137/515.5 |
| 4,809,679 A | 3/1989 | Shimonaka et al. | 128/4 |
| 4,816,020 A | 3/1989 | Brownell | 604/97 |
| 4,819,684 A | 4/1989 | Zaugg et al. | 137/112 |
| 4,850,978 A | 7/1989 | Dudar et al. | 604/201 |
| 4,874,377 A | 10/1989 | Newgard et al. | 604/167 |
| 4,915,687 A | 4/1990 | Sivert | 604/83 |
| 4,917,668 A | 4/1990 | Haindl | 604/167 |
| 4,935,010 A | 6/1990 | Cox et al. | 604/122 |
| 4,966,199 A | 10/1990 | Ruschke | 137/843 |
| 5,006,114 A | 4/1991 | Rogers et al. | 604/167 |
| 5,041,087 A | 8/1991 | Loo et al. | 604/83 |
| 5,048,537 A | 9/1991 | Messinger | 128/673 |
| 5,049,128 A | 9/1991 | Duquette | 604/83 |
| 5,059,175 A | 10/1991 | Hanover et al. | 604/891.1 |
| 5,065,783 A | 11/1991 | Ogle, II | 137/68.1 |
| 5,080,654 A | 1/1992 | Picha et al. | 604/167 |
| 5,085,645 A | 2/1992 | Purdy et al. | 604/167 |
| 5,100,394 A | 3/1992 | Dudar et al. | 604/283 |
| 5,108,380 A | 4/1992 | Herlitze et al. | 604/283 |
| 5,147,333 A | 9/1992 | Raines | 604/249 |
| 5,171,230 A | 12/1992 | Eland et al. | 604/250 |
| 5,171,239 A | 12/1992 | Igaue et al. | 604/385.2 |
| 5,199,947 A | 4/1993 | Lopez et al. | 604/56 |
| 5,201,715 A | 4/1993 | Masters | 604/175 |
| 5,203,775 A | 4/1993 | Frank et al. | 604/256 |
| 5,215,538 A | 6/1993 | Larkin | 604/249 |
| 5,221,271 A | 6/1993 | Nicholson et al. | 604/283 |
| 5,230,706 A | 7/1993 | Duquette | 604/83 |
| 5,242,393 A | 9/1993 | Brimhall et al. | 604/86 |
| 5,242,432 A | 9/1993 | DeFrank | 604/284 |
| 5,269,771 A | 12/1993 | Thomas et al. | 604/213 |
| 5,280,876 A | 1/1994 | Atkins | 251/149.1 |
| 5,300,034 A | 4/1994 | Behnke et al. | 604/167 |
| 5,320,328 A | 6/1994 | Decloux et al. | 251/326 |
| 5,330,435 A | 7/1994 | Vaillancourt | 604/167 |
| 5,349,984 A | 9/1994 | Weinheimer et al. | 137/543.21 |
| 5,360,413 A | 11/1994 | Leason et al. | 604/249 |
| 5,380,306 A | 1/1995 | Brinon | 604/244 |
| 5,390,898 A | 2/1995 | Smedley et al. | 251/149.6 |
| 5,401,255 A | 3/1995 | Sutherland et al. | 604/247 |
| 5,439,451 A | 8/1995 | Collinson et al. | 604/247 |
| 5,465,938 A | 11/1995 | Werge et al. | 251/149.1 |
| 5,474,536 A | 12/1995 | Bonaldo | 604/86 |
| 5,474,544 A | 12/1995 | Lynn | 604/283 |
| 5,485,640 A | 1/1996 | Workman | 5/263 |
| 5,509,433 A | 4/1996 | Paradis | 137/1 |
| 5,509,912 A | 4/1996 | Vaillancourt et al. | 604/283 |
| 5,520,666 A | 5/1996 | Choudhury et al. | 604/283 |
| 5,533,708 A | 7/1996 | Atkinson et al. | 251/149.1 |
| 5,533,983 A | 7/1996 | Haining | 604/249 |
| 5,549,566 A | 8/1996 | Elias et al. | 604/167 |
| 5,569,209 A | 10/1996 | Roitman | 604/190 |
| 5,569,235 A | 10/1996 | Ross et al. | 604/403 |
| 5,573,516 A | 11/1996 | Tyner | 604/249 |
| 5,578,059 A | 11/1996 | Patzer | 604/249 |
| 5,616,129 A | 4/1997 | Mayer | 604/167 |
| 5,616,130 A | 4/1997 | Mayer | 604/167 |
| 5,620,434 A | 4/1997 | Brony | 604/406 |
| 5,674,206 A | 10/1997 | Allton et al. | 604/249 |
| 5,676,346 A | 10/1997 | Leinsing | 251/149.1 |
| 5,685,866 A | 11/1997 | Lopez | 604/249 |
| 5,694,686 A | 12/1997 | Lopez | 29/890.126 |
| 5,695,466 A | 12/1997 | Lopez et al. | 604/93 |
| 5,699,821 A | 12/1997 | Paradis | 137/1 |
| 5,700,248 A | 12/1997 | Lopez | 604/249 |
| 5,730,418 A | 3/1998 | Feith et al. | 251/149.6 |
| 5,749,861 A | 5/1998 | Guala et al. | 604/249 |
| RE35,841 E | 7/1998 | Frank et al. | 604/256 |
| 5,806,831 A | 9/1998 | Paradis | 251/149.1 |
| 5,820,601 A | 10/1998 | Mayer | 604/167 |
| 5,921,264 A | 7/1999 | Paradis | 137/15 |
| 6,029,946 A | 2/2000 | Doyle | 251/149.1 |
| 6,036,171 A | 3/2000 | Weinheimer et al. | 251/149.1 |
| 6,039,302 A * | 3/2000 | Cote et al. | 251/149.1 |
| 6,048,335 A | 4/2000 | Mayer | 604/167 |
| 6,050,978 A * | 4/2000 | Orr et al. | 604/249 |
| 6,063,062 A | 5/2000 | Paradis | 604/249 |
| 6,068,011 A | 5/2000 | Paradis | 137/1 |
| 6,079,432 A | 6/2000 | Paradis | 137/1 |
| 6,089,541 A | 7/2000 | Weinheimer et al. | 251/149.6 |
| 6,142,446 A * | 11/2000 | Leinsing | 251/149.1 |
| 6,152,900 A | 11/2000 | Mayer | 604/167 |
| 6,228,069 B1 | 5/2001 | Barth et al. | 604/249 |
| 6,245,048 B1 | 6/2001 | Fangrow, Jr. et al. | 604/249 |
| 6,290,206 B1 * | 9/2001 | Doyle | 251/149.1 |
| 6,344,033 B1 | 2/2002 | Jepson et al. | 604/256 |
| 6,428,520 B1 | 8/2002 | Lopez et al. | 604/249 |
| 6,543,745 B1 | 4/2003 | Enerson | 251/149.7 |
| 6,595,964 B2 | 7/2003 | Finley et al. | 604/246 |
| 6,609,696 B2 | 8/2003 | Enerson | 251/86 |
| 6,669,673 B2 | 12/2003 | Lopez | 604/249 |
| 6,706,022 B1 * | 3/2004 | Leinsing et al. | 604/247 |

| | | | |
|---|---|---|---|
| 6,883,778 B1 * | 4/2005 | Newton et al. ............ 251/149.1 |
| 2003/0050610 A1 | 3/2003 | Newton et al. .............. 604/256 |
| 2003/0093061 A1 | 5/2003 | Ganem ........................ 604/533 |
| 2003/0098430 A1 | 5/2003 | Leinsing et al. ........... 251/149.6 |
| 2003/0141477 A1 | 7/2003 | Miller ..................... 251/149.1 |
| 2004/0073171 A1 | 4/2004 | Rogers et al. .......... 604/164.13 |

FOREIGN PATENT DOCUMENTS

| | | |
|---|---|---|
| EP | 0629418 A1 | 12/1994 |
| EP | 1243285 | 9/2002 |
| GB | 2 079 162 | 1/1982 |
| WO | 83/02559 | 8/1983 |
| WO | 93/11828 | 6/1993 |
| WO | 96/00107 | 1/1996 |
| WO | 97/39791 | 10/1997 |
| WO | 98/22178 | 5/1998 |
| WO | WO 98/22178 | 5/1998 |
| WO | WO 98/26835 | 6/1998 |
| WO | WO 9826835 A1 * | 6/1998 |
| WO | 98/39594 | 9/1998 |
| WO | 00/44433 | 8/2000 |
| WO | WO 01 20218 A1 | 3/2001 |
| WO | WO 03/018104 A2 | 3/2003 |
| WO | WO 03/018105 A1 | 3/2003 |
| WO | WO 2004/060466 | 7/2004 |

* cited by examiner

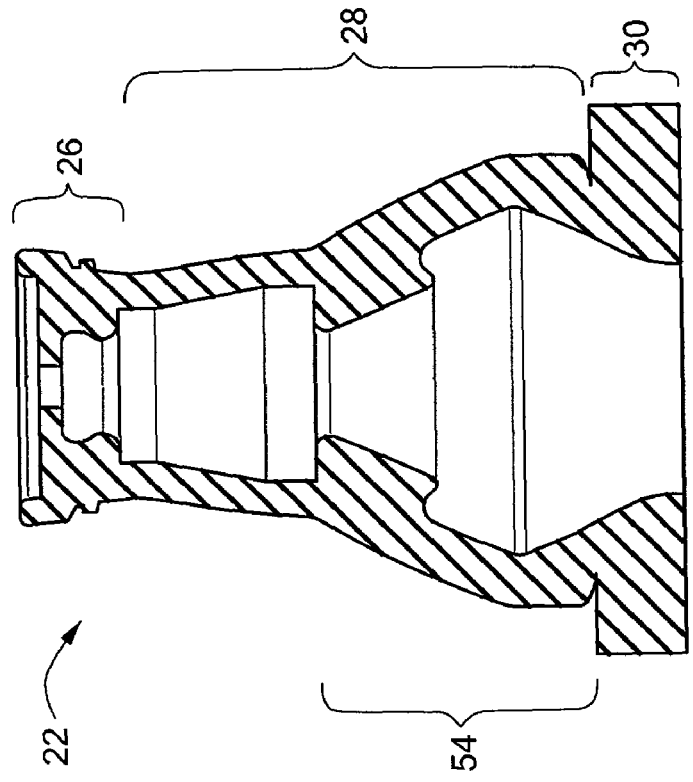
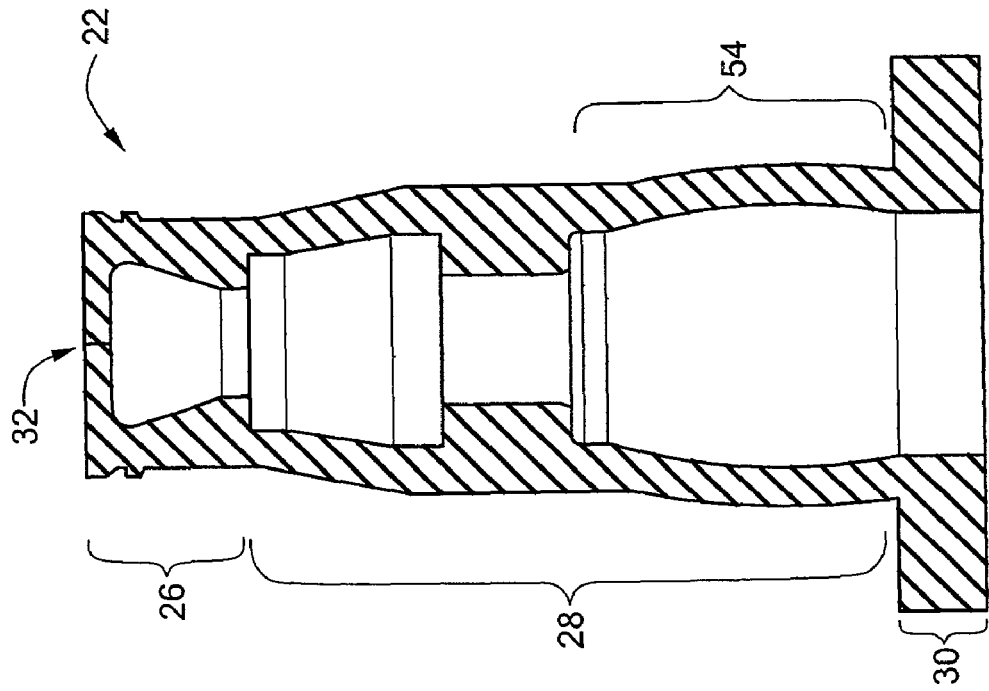
FIG. 4B
FIG. 4A

MEDICAL VALVE WITH EXPANDABLE MEMBER

PRIORITY

This patent application claims priority from provisional U.S. patent application No. 60/314,210, filed Aug. 22, 2001, and entitled, "MEDICAL VALVE WITH VARIABLE VOLUME CHAMBER," the disclosure of which is incorporated herein, in its entirety, by reference.

FIELD OF THE INVENTION

The invention generally relates to medical valves and, more particularly, the invention relates to reducing backflow through medical valves.

BACKGROUND OF THE INVENTION

Medical valving devices typically valve fluids injected into and withdrawn from a patient. One exemplary type of medical valving device, known in the art as a "catheter introducer," maintains a sealed port for accessing the patient's vasculature. Use of such a valve enables vascular access without requiring the patient's skin to be repeatedly pierced by a needle. Moreover, catheter introducers are constructed to withstand a range of back-pressures produced by a patient's blood pressure, thus minimizing blood loss resulting from fluid injections or withdrawals.

Fluid commonly is transferred to/from a patient by inserting a syringe into a medical valve, thus communicating with the patient's vasculature. Problems arise, however, when the syringe is withdrawn from the valve. More particularly, a back pressure (i.e., a proximally directed pressure) produced by the withdrawing syringe undesirably can cause blood to leak proximally into various parts of the valve. In addition to coagulating and impeding the mechanical operation of the valve, blood in the valve also compromises the sterility of the valve.

The art has attempted to minimize fluid drawback by forcibly reducing the volume of an interior fluid chamber when the valve is closed. In particular, one such type of valve aimed at solving this problem has extra mechanical parts to compress a member that defines such a fluid chamber. See, for example, U.S. Pat. No. 5,921,264 (Paradis), which requires additional cantilever fingers and other cooperating mechanical parts to purportedly accomplish this function.

In addition to requiring more parts for this purpose, another type of valve forces a compressible member into a reduced diameter lumen, consequently forcibly reducing the volume of the fluid chamber. See, for example, U.S. Pat. No. 6,152,900 (Mayer), which uses this technique to purportedly solve the drawback problem.

Both noted purported solutions create additional problems. In particular, adding more parts increases the manufacturing cost of the valve. For example, more parts typically increases material cost, assembly time, and testing time. Moreover, the additional parts must cooperate in a proper manner to ensure that the valve operates as intended. In other words, a defect in one of the additional parts can adversely affect the mechanical operation of the valve. Furthermore, accurately forcing a compressible member into a reduced diameter lumen after such member has expanded can be difficult, thus possibly rendering the valve unusable.

SUMMARY OF THE INVENTION

In accordance with one aspect of the invention, a medical valve has a resilient member that is forcibly expanded to an expanded volume from a normal volume. Specifically, the valve operates in a closed mode that prevents fluid flow, and an open mode that permits fluid flow. To these ends, the valve has a housing having an inlet and an outlet, and the noted resilient member within the housing. The resilient member and housing form a fluid channel between the inlet and the outlet. The fluid channel at least in part extends through the resilient member. The fluid channel has a given portion formed by a variable volume portion of the resilient member. The variable volume portion has a normal volume when in the closed mode, and an expanded volume when the open mode. The expanded volume is greater than the normal volume.

In illustrative embodiments, the housing and variable volume portion form a space when in the closed mode. The variable volume portion is free to expand into the space when the valve transitions from the closed mode to the open mode. The volume of the variable volume portion may expand as the valve transitions from the closed mode to the open mode.

The variable volume portion may enlarge in response to receipt of a distally directed force. The variable volume portion of the resilient member also has an inner dimension, where the distally directed force causes the inner dimension of the variable volume portion to expand radially as the valve transitions toward the open mode.

In some embodiments, the resilient member includes a proximal portion located proximal of the variable volume portion. The proximal portion has a swabbable portion. The valve further may have a plug member that also forms the fluid channel. The plug member cooperates with the resilient member to form a flow controller that controls fluid flow through the valve. The flow controller is activated by a blunt tip. The variable volume portion of the resilient member illustratively has the normal volume when no radially compressive forces are applied to it. In some embodiments, the variable volume portion is formed from a resilient material having a relaxed state when no more than a negligible force is applied to it. The variable volume portion has the normal volume when in the relaxed state.

In accordance with another aspect of the invention, a medical valve operating at and between a closed mode and an open mode has an inlet, an outlet, and a fluid channel between the inlet and the outlet. The valve also includes a resilient member between the inlet and outlet, where the resilient member forms a given portion of the fluid channel. The resilient member has a variable volume portion that forms the given portion of the fluid channel. The variable volume portion is defined by a resilient wall that causes the variable volume portion to have a normal volume when in the closed mode. The wall causes the variable volume portion to have an enlarged volume when in the open mode, where the enlarged volume is greater than the normal volume. The wall is forced radially outwardly from a relaxed state as the valve transitions from the closed mode toward the open mode.

In illustrative embodiments, the wall is in the relaxed state when it receives no more than a negligible force. The wall may be forced radially outwardly in response to receipt of a distally directed force. The valve also may include a housing that contains the resilient member. The housing has an inner surface spaced from the wall when in the closed mode. The inner surface and wall form a space into which the wall is free to expand when the valve transitions toward the open mode.

In accordance with other aspects of the invention, a medical valve having a closed mode and an open mode includes a housing having an inlet and an outlet, and a resilient member within the housing. The resilient member and housing form a fluid channel between the inlet and the outlet, where the fluid channel at least in part extends through the resilient member. The fluid channel has a given portion formed by a variable volume portion of the resilient member. The variable volume portion has a closed mode volume when in the closed mode. Moreover, the variable volume portion is flexed to have an open mode volume when in the open mode. The open mode volume is greater than the closed mode volume.

BRIEF DESCRIPTION OF THE DRAWINGS

The foregoing and advantages of the invention will be appreciated more fully from the following further description thereof with reference to the accompanying drawings wherein:

FIGS. 4A and 4B respectively schematically show a gland member in a closed mode and an open mode.

DESCRIPTION OF ILLUSTRATIVE EMBODIMENTS

In illustrative embodiments of the invention, a medical valve is configured to substantially eliminate fluid drawback when a nozzle or syringe is withdrawn from it. In fact, in some embodiments, the valve is expected to produce a positive, distally directed pressure when a nozzle or syringe is withdrawn. Such pressure necessarily should prevent non-negligible amounts of fluid from being drawn into the valve.

To these ends, illustrative embodiments of the medical valve have an interior fluid chamber that is larger when it is in an open mode (i.e., permitting fluid flow, also referred to as "open position"), than when it is in a closed mode (i.e., preventing fluid flow, also referred to as "closed position"). More specifically, the fluid chamber is formed from a resilient member that, when transitioning from the closed mode toward the open mode, expands from its normal (i.e., relaxed) state. This expansion consequently increases the volume of fluid that the fluid chamber can contain when in the open mode. Accordingly, when retracting back to the closed mode, the resilient member returns to its normal state, which has a smaller volume. Excess fluid within the fluid chamber thus is forced out the distal end of the valve as the valve transitions toward the closed mode. Accordingly, fluid should not be drawn into the valve when withdrawing a syringe. Details of illustrative embodiments are discussed below.

Figure 1:
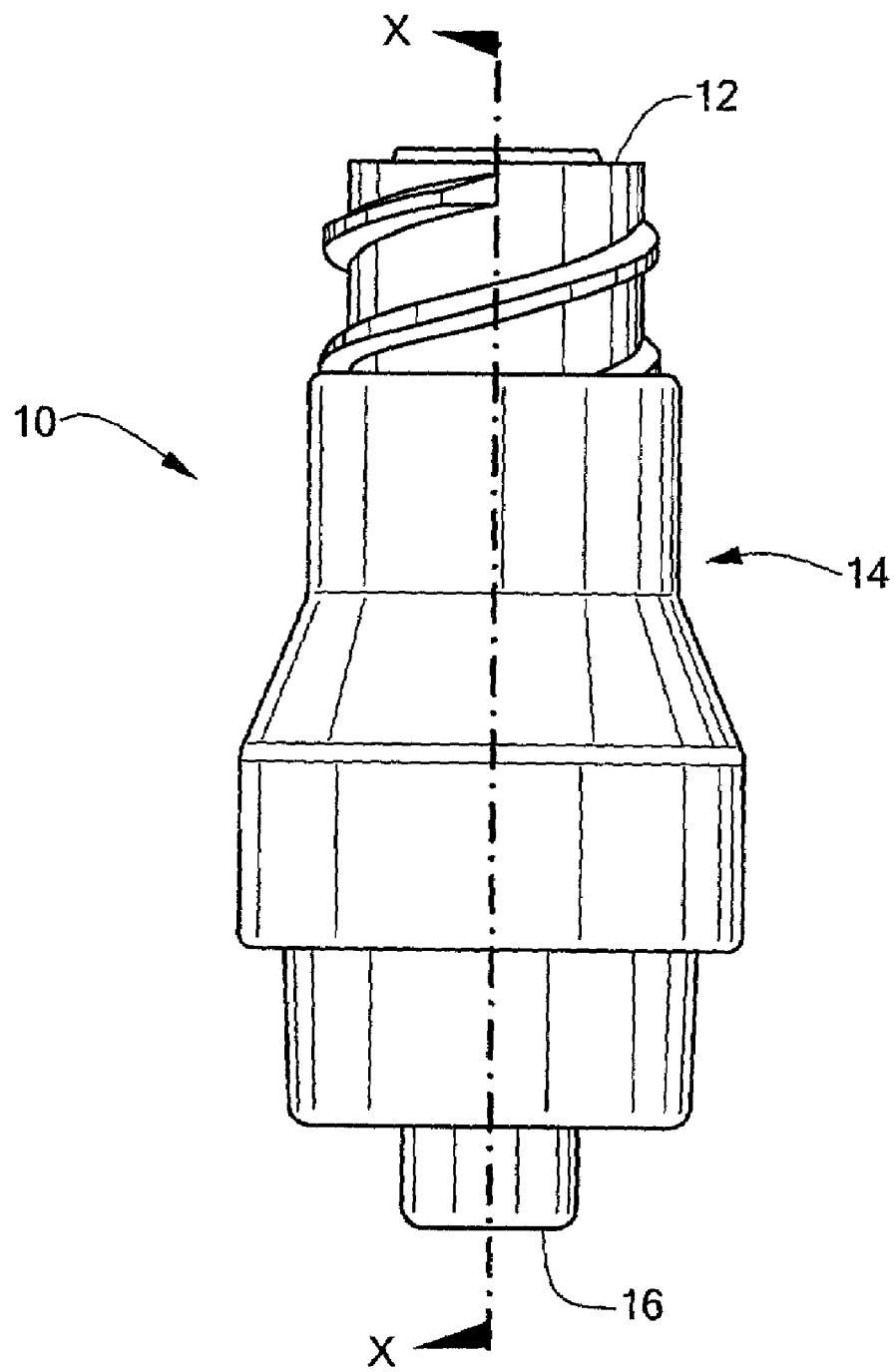
FIG. 1 schematically shows a medical valve configured in accordance with illustrative embodiments of the invention.

FIG. 1 schematically shows a medical valve 10 that is configured to reduce fluid drawback (a/k/a "back-flow," noted above) when a syringe or other type of nozzle is withdrawn from it. The valve 10 includes a proximal port 12 (also referred to herein as "inlet 12") for receiving the nozzle, a valve body/housing 14 having a valving mechanism (shown in FIGS. 2-6) that controls fluid flow through the valve 10, and a distal port 16 (also referred to herein as outlet 16) for directing fluid between the valve 10 and a patient. The fluid preferably is in liquid form, such as liquid medication, to pass through a centrally formed fluid channel (discussed in greater detail below). Although much of the discussion herein refers to the proximal port 12 as a fluid inlet, and the distal port 16 as a fluid outlet, the proximal and distal ports 12 and 16 also may be respectively used as outlet and inlet ports.

In illustrative embodiments, the valve 10 is similar to the swab valve disclosed in U.S. Pat. No. 6,039,302 entitled, "SWABBABLE LUER-ACTIVATED VALVE," the disclosure of which is incorporated herein, in its entirety, by reference. Of course, various embodiments may relate to other non-swab valves and thus, such embodiments are not limited to swab valves.

Figure 2:
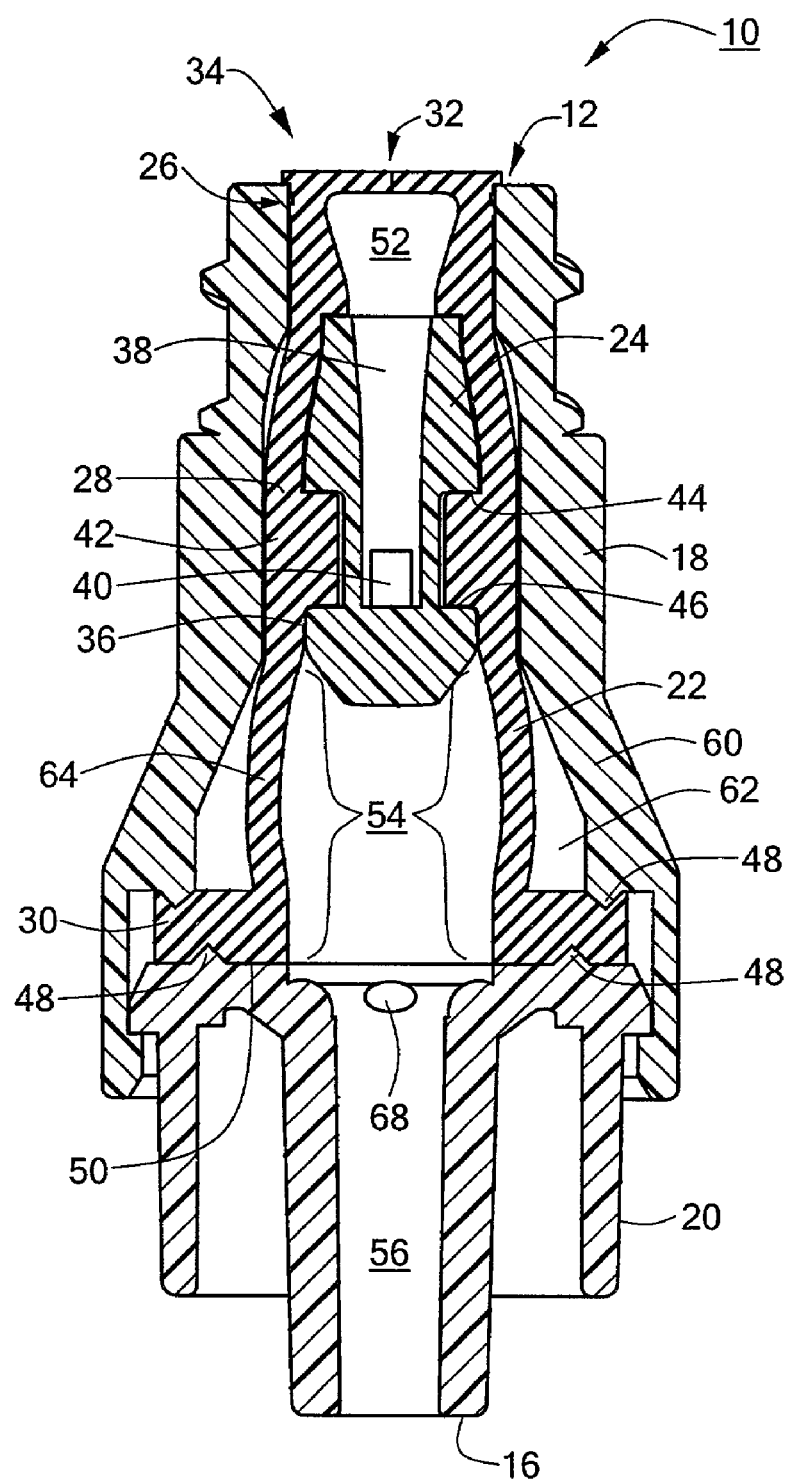
FIG. 2 schematically shows one embodiment of the medical valve shown in FIG. 1 along line X-X.
Figure 3:
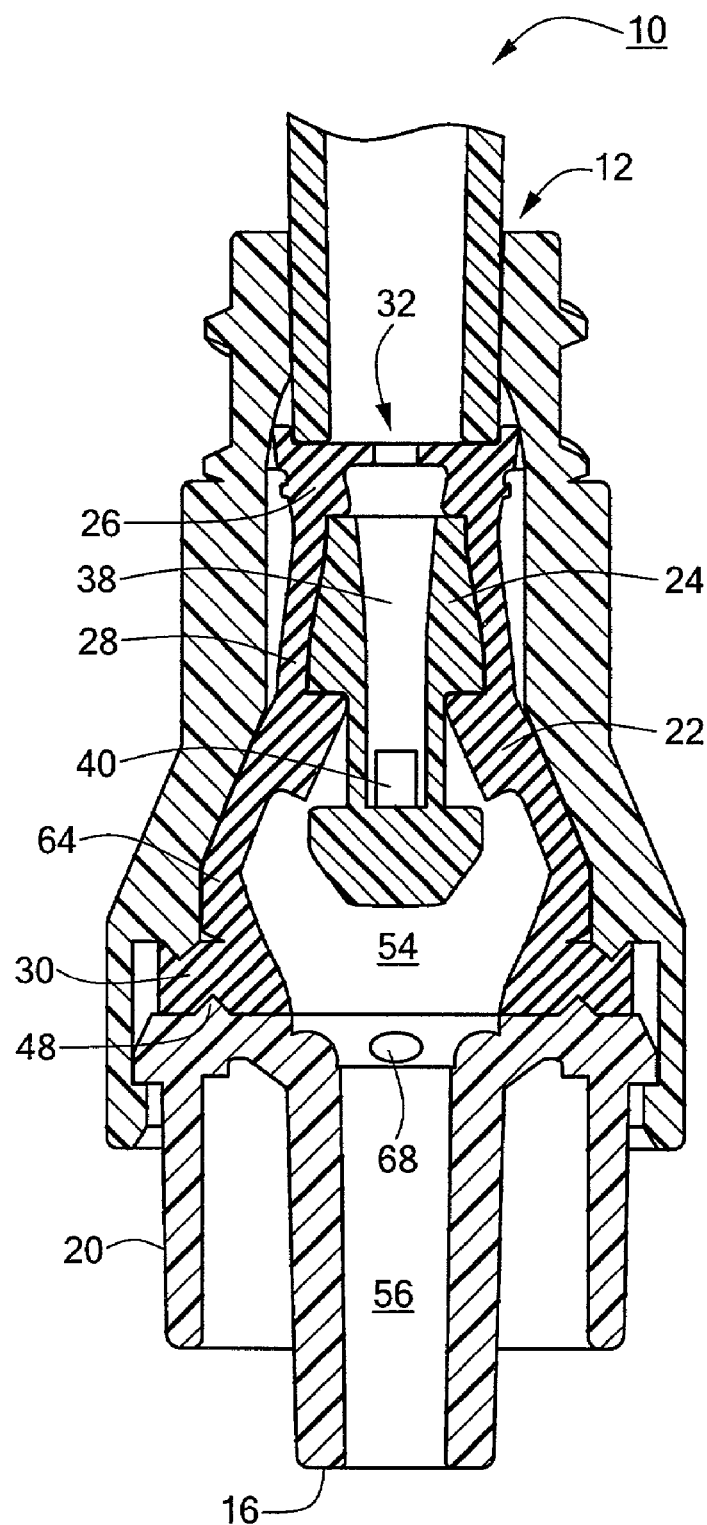
FIG. 3 schematically shows the medical valve in FIG. 2 in an open mode.

FIG. 2 schematically shows a cross-sectional view of one embodiment of the medical valve 10 (shown in FIG. 1 along line X-X) in a closed mode. FIG. 3 similarly shows a cross-sectional view of the same valve 10, but in an open mode. In summary, the valve 10 includes four snap-fit components. Specifically, the valve 10 includes an inlet housing 18 having the inlet 12, and an outlet housing 20 having the outlet 16. The two housing portions 18 and 20 together form the valve body/housing 14. The remaining two components cooperate to valve fluid through the housing 14. Specifically, the valve 10 also has a stretchable, resilient, and compressible member (referred to in various embodiments herein as "gland 22") secured between the inlet housing 18 and outlet housing 20, and a rigid, longitudinally movable plug 24 (also more generally referred to as a "plug member" due in part to its plugging function) secured within the valve 10 by the gland 22. Details of these four valve components and their cooperation are discussed below.

The first of these components to be discussed, gland 22, is considered to have three contiguous sections. In particular, those sections include a proximally located swabbable seal section 26 to provide a low pressure, proximally located seal, a tubular section 28 that cooperates with the plug 24 to control fluid flow, and an attachment section 30 to secure the gland 22 within the valve 10. Each of these sections are discussed below.

More specifically, the seal section 26 has a normally closed aperture 32 to provide the above noted low pressure seal. Among other things, the aperture 32 may be, for example, a pierced hole or a slit. A nozzle or syringe thus may open the seal by deforming the seal section 26.

The aperture 32 illustratively is formed to be normally closed when the valve 10 is in the closed mode. No radial force thus is required by the housing to close the aperture 32. In fact, in some embodiments, the outer diameter of the seal section 26 is smaller than the inner diameter of the inlet 12. In alternative embodiments, however, the inner diameter of the inlet 12 is smaller than the outer diameter of the seal section 26 of the gland 22. Consequently, in such embodiments, the housing squeezes the seal section 26, thereby forcing the aperture 32 closed.

When the valve 10 is in the fully closed position, the seal section 26 is flush with, or extends slightly above, the exterior inlet face 34 of the housing. The seal section 26 and the exterior inlet face 34 thus present a swabbable surface. In other words, the seal section 26 and the exterior inlet face 34 may be easily wiped clean by any conventional means, such as with an alcohol swab. As mentioned in the above noted incorporated patent, valves having swabbable surfaces are known in the art as "swabbable valves." In other embodiments, however, the valve 10 is not a swabbable valve.

The second section of the gland 22, the tubular section 28, illustratively is both resilient and compressible. Accordingly, the tubular section 28 effectively acts as a spring to normally maintain the gland 22 in the closed mode. In addition, the tubular section 28 also cooperates with the plug 24 to provide a high pressure seal area 36. Specifically, the plug 24 has a plug flow channel 38 that makes up a portion of the overall fluid channel 52 through the valve 10 (discussed below). The plug flow channel 38 terminates at a lo transverse channel 40 that normally is occluded by the tubular section 28 (see FIG. 2). To that end, the outer diameter of the outlet end of the plug 24 is selected to match the inner diameter of a sealing portion of the gland 22 when in the closed mode. For example, the plug outlet end 46 may have a wider outer diameter than the inner diameter of the compressible, tubular section 28 of the gland 22. This high pressure seal area 36 thus is able to resist a large amount of back pressure from the outlet end of the valve 10. Moreover, since the valve 10 has this high pressure seal area 36, it is not necessary for the low pressure seal (i.e., the aperture 32 through the seal section 26) to resist large back pressures.

A portion of the tubular section 28 illustratively is preloaded by having a preload gland portion 42 that is slightly longer (when in its normal state) than the distance between a plug ledge 44 and the plug outlet end 46. For example, when in its normal state, the preload gland portion 42 may be about 0.005 inches longer than the noted plug distance. This preloading ensures that the preload gland portion 42 of the tubular section 28 is under compression in all modes/states. Consequently, the transverse channel 40 should be properly located relative to the tubular section 28 to maintain the high pressure seal area 36. Accordingly, preloading ensures that the high pressure seal area 36 maintains its sealing function. The valve 10 thus should resist opening in response to either a positive pressure or a negative pressure applied to the outlet 16.

The final one of the above listed gland sections, the attachment section 30, serves several important functions. Primarily, it secures the gland 22 within the housing. To that end, the housing includes a pair of opposed annular upstanding ridges 48 that normally are forced into the proximal and distal surfaces of the attachment section 30. In addition, the attachment section 30 rests on a relatively flat inner surface of the housing 50, thus providing a base from which the tubular section 28 can provide its spring (i.e., proximal biasing) functionality.

As noted above, the gland 22, plug 24, and housing 14 together form the above noted fluid channel 52 extending from the inlet 12 to the outlet 16. Accordingly, when in the open mode, fluid can flow (via a nozzle) through the following structures (in the noted order), which as a whole make up the entire fluid channel 52:

the inlet 12;
the seal section 26 of the gland 22;
the plug flow channel 38 (including the transverse channel 40);
a variable volume chamber 54, which is a part of the tubular section 28 of the gland 22 (see discussion immediately below);
a distal portion 56 of the housing; and
the outlet 16.

In illustrative embodiments, this fluid channel 52 is specially configured to expand when the valve 10 transitions toward the open mode, and relax (i.e., contract) when the valve 10 transitions toward the closed mode. To that end, the tubular section 28 of the gland 22 includes a distal portion that forms the above noted variable volume chamber (identified generally by reference number 54). The chamber 54 illustratively is spaced (producing space 62) from the internal walls 60 of the housing 14. Accordingly, as shown in FIG. 3 and discussed below, the variable volume chamber 54 may expand into the space 62 as the valve 10 transitions between the closed mode and the open mode.

The variable volume chamber 54 is an integral portion of the gland 22 and thus, manufactured from the same material. In illustrative embodiments, the gland 22 is manufactured from an elastomeric material that is both resilient and flexible. For example, the gland 22 may be made from medical grade silicon or rubber. A slightly bowed circumferential wall 64 defines the volume that comprises the chamber 54. More specifically, FIG. 4A schematically shows a cross-section of the gland 22 in its normal, relaxed state (i.e., during the closed mode), while FIG. 4B schematically shows a cross-section of the gland 22 in its stressed state (i.e., during the open mode, or as it transitions toward the open mode). As shown in the figures, the wall 64 is molded to be slightly bowed outwardly. This slight bowing should facilitate expansion of the wall 64 when a distally directed force is applied to the valve 10. In some embodiments, however, the wall 64 is not outwardly bowed (see, for example, the embodiment shown in FIGS. 5 and 6, discussed below). The wall 64 may be referred to herein as means for expanding.

It should be noted that the variable volume chamber 54 is considered to be in a "normal" state when no more than a negligible force is applied to it. When in the normal state, the variable volume chamber 54 is considered to have a "normal" volume. Among other things, negligible force may include the weight of supporting the plug (when no nozzle is inserted in the valve 10), the force of gravity, the effect of the plug preload on the chamber 54, or the forces applied by different sections of the housing (e.g., at the upstanding ridge). In other words, the variable volume chamber 54 is considered to be in its normal state when it is not forced to a shape/size other than that which it was originally molded. No compressive or expansive forces are applied. Accordingly, the chamber 54 is in its normal state (i.e., relaxed) when in the closed mode (e.g., see FIG. 4A). Conversely, the chamber 54 is not in its normal state when it is transitioning to or from the open mode (e.g., see FIG. 4B).

In illustrative embodiments, the volume of the chamber 54 changes as the plug 24 longitudinally moves proximally and distally within the valve 10. Of course, plug movement is caused in response to insertion of the nozzle. Accordingly, as the plug 24 moves distally (i.e., by a distally directed longitudinal force applied by the nozzle), at least a portion of the wall 64 of the chamber 54 is urged in a radially outward direction toward the internal walls 60 of the inlet housing 18 (see FIG. 3). In other words, at least a portion of the wall 64 of the chamber 54 is forced (i.e., by flexing) from its normal (i.e., relaxed) state. This causes the chamber 54 to have a larger volume than when the valve 10 is in the closed mode. Stated another way, an inner dimension of the chamber 54 increases as the nozzle is inserted into the valve 10. In a corresponding manner, as the plug moves proximally from the open mode, the chamber 54 volume decreases, thus forcing fluid from the chamber 54. Since fluid is being forced from the chamber 54, fluid should not be drawn into any part of the valve 10.

The longitudinal force applied to the gland 22 by the outlet end 46 of the plug 24 should cause the chamber 54 to radially expand. In some embodiments, however, a mechanical assist also may be included to more directly cause the gland to radially expand. For example, such mechanical assist may be similar to that disclosed in co-pending provisional U.S. patent application No. 60/350,775, filed Jan. 22, 2002, the disclosure of which is incorporated herein, in its entirety, by reference.

In alternative embodiments, the chamber 54 may have some initial compression when in the closed mode. In such case, however, at least a portion of the wall 64 of the chamber 54 is forced radially outwardly in a manner similar to the other described embodiments. In various embodiments, the volume of the chamber 54 does not increase and decrease linearly. Notwithstanding this result, the volume of the chamber 54 is larger in the open mode than when in the closed mode.

Figure 5:
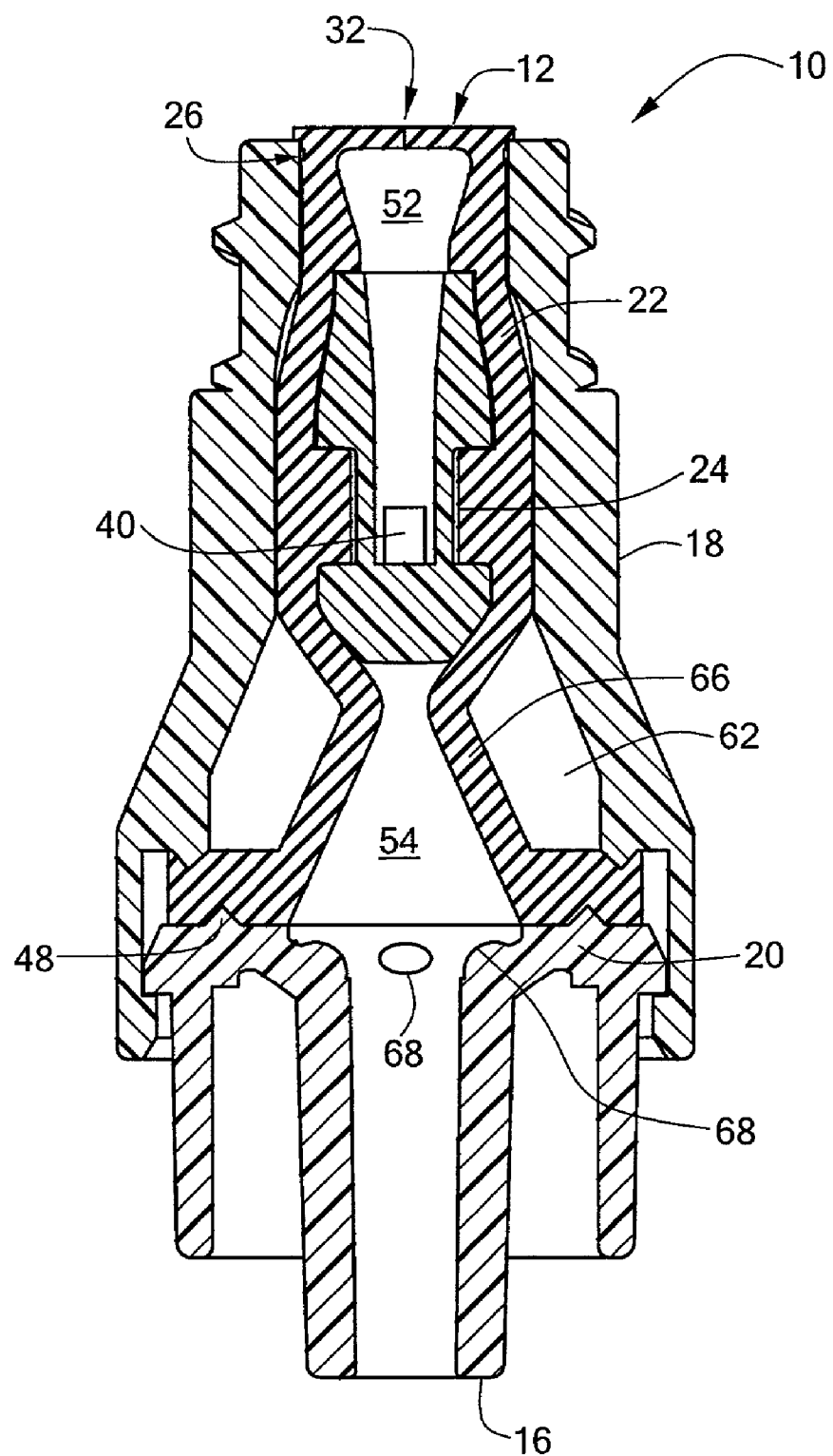
FIG. 5 schematically shows another embodiment of the medical valve shown in FIG. 1 along line X-X.
Figure 6:
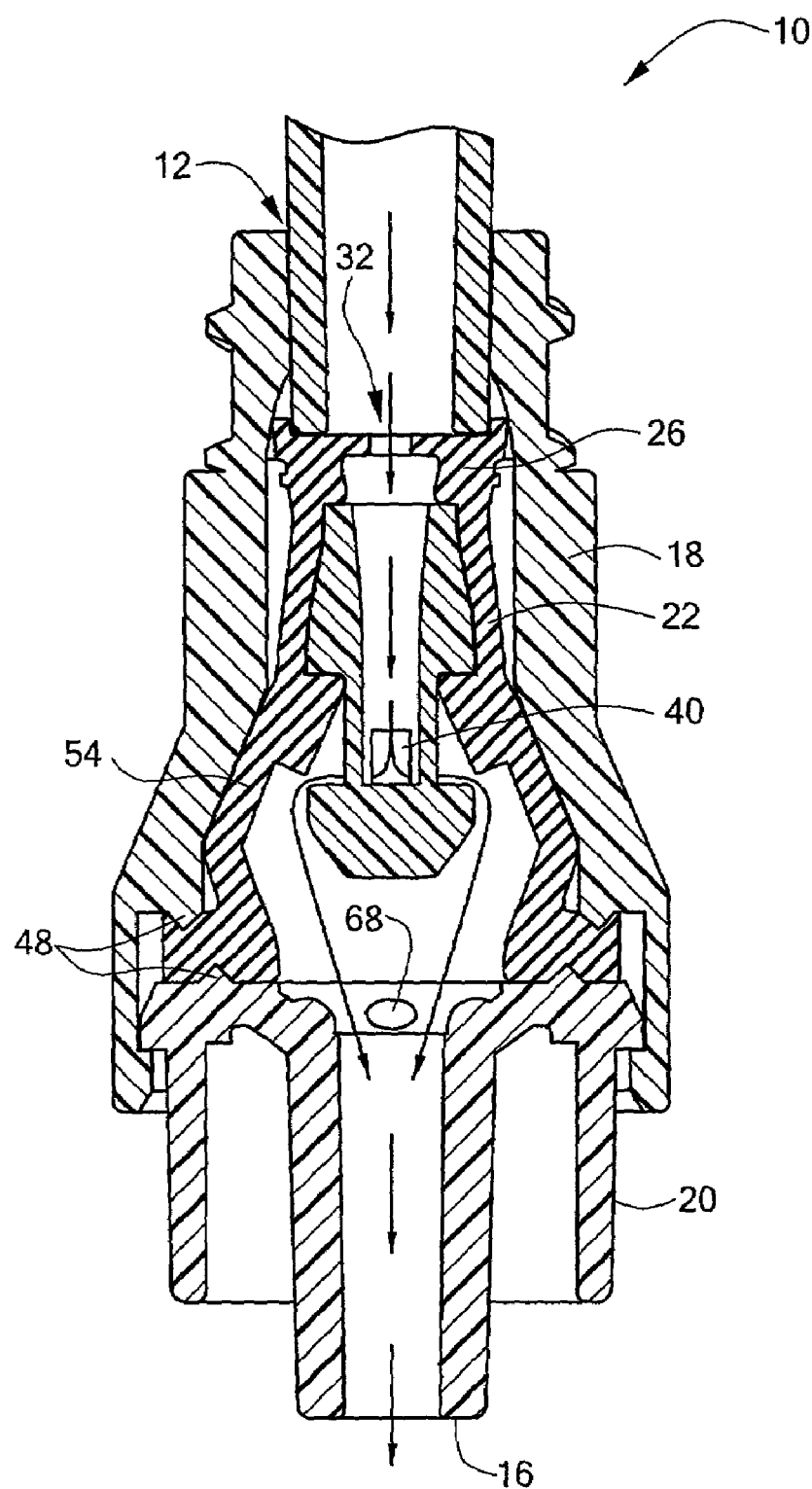
FIG. 6 schematically show the medical valve in FIG. 5 in an open mode.

FIG. 5 schematically shows a cross-sectional view of another embodiment of the medical valve 10 (shown in FIG. 1 along line X-X) in a closed mode. FIG. 6 similarly shows a cross-sectional view of the same embodiment of the valve 10, but in an open mode. In this embodiment, the portion of the attachment section 30 that forms the chamber 54 has a part that tapers inwardly (shown at reference number 66). For example, the chamber wall 64 may have opposing tapering sections. Accordingly, the (bulbous) distal end of the plug 24 applies a direct radially outward force to the interior wall 64 of the gland 22, thus prying the gland 22 in that direction. The combination of this force and the distally directed force of the distally moving plug 24 urges the distal gland portion in a radially outward direction. As shown in FIG. 6, the chamber 54 expands substantially to the inner walls of the inlet housing 18, thus enlarging the volume of the chamber 54. In a similar manner to the embodiment shown in FIGS. 2 and 3, the chamber 54 is larger when the valve 10 is in the open mode than when the valve 10 is in the closed mode.

The valve 10 may include additional features. Specifically, the valve 10 may include a stop 68 to prevent the plug from extending too far into the chamber 54. Further features may be those included in above noted U.S. Pat. No. 6,039,302.

It should be noted that although illustrative embodiments are discussed as being snap fit together, alternative embodiments may be coupled by other known means. For example, the inlet housing 18 may be ultrasonically shear welded to the outlet housing 20 in accordance with conventional welding techniques. When coupled by any method, however, the gland 22 may be secured between the inlet and outlet housings 18 and 20 and by the ridges 48 that extend directly into the gland 22. In alternative embodiments, the gland 2; is not secured between the inlet and outlet housings 18 and 20. It also is expected that in addition to being activated (i.e., opened) by a blunt tipped apparatus (e.g., a luer tip or nozzle), various embodiments may be activated by a needled syringe.

Although various exemplary embodiments of the invention are disclosed below, it should be apparent to those skilled in the art that various changes and modifications can be made that will achieve some of the advantages of the invention without departing from the true scope of the invention.

What is claimed is:

1. A medical valve having a closed mode that prevents fluid flow, the medical valve also having an open mode that permits fluid flow, the medical valve comprising:
   a housing having an inlet and an outlet;
   a resilient member within the housing, the resilient member and housing forming a fluid channel between the inlet and the outlet, the fluid channel at least in part extending through the resilient member,
   the fluid channel having a given portion formed by a variable volume portion of the resilient member, the variable volume portion being in fluid communication with the outlet, the variable volume portion having a normal volume when in the closed mode, the variable volume portion having an expanded volume when in the open mode, the expanded volume being greater than the normal volume; and
   a moveable plug member being located entirely within the resilient member during both the closed and open modes, the moveable plug member being longitudinally moveable as the valve transitions between the open and closed modes.

2. The medical valve as defined by claim 1 wherein the housing and variable volume portion form a space when in the closed mode, the variable volume portion being free to expand into the space when the valve transitions from the closed mode to the open mode.

3. The valve as defined by claim 1 wherein the volume of the variable volume portion expands as the valve transitions from the closed mode to the open mode.

4. The valve as defined by claim 1 wherein the variable volume portion enlarges in response to receipt of a distally directed force.

5. The valve as defined by claim 4 wherein the variable volume portion of the resilient member has an inner dimension, the distally directed force causing the inner dimension of the variable volume portion to expand radially as the valve transitions toward the open mode.

6. The valve as defined by claim 1 wherein the resilient member includes a proximal portion located proximal of the variable volume portion, the proximal portion having a swabbable portion.

7. The valve as defined by claim 1 wherein the plug member also forms the fluid channel, the plug member cooperating with the resilient member to form a flow controller that controls fluid flow through the valve, the flow controller being activated by a blunt tip.

8. The valve as defined by claim 1 wherein the variable volume portion of the resilient member has the normal volume when no radially compressive forces are applied to it.

9. The valve as defined by claim 1 wherein the variable volume portion is formed from a resilient material, the resilient material having a relaxed state when no more than a negligible force is applied to it, the variable volume portion having the normal volume when in the relaxed state.

10. A medical valve having a closed mode that prevents fluid flow, the medical valve also having an open mode that permits fluid flow, the medical valve comprising:
    a housing having an inlet and an outlet;
    a resilient member within the housing, the resilient member and housing forming a fluid channel between the inlet and the outlet, the fluid channel at least in part extending through the resilient member,
    the resilient member having means for expanding from a normal volume, wherein the resilient member includes a proximal portion located proximal of the expanding means, the proximal portion having a swabbable portion,
    the fluid channel having a given portion formed by the expanding means, the expanding means being in fluid communication with the outlet, the expanding means having the normal volume when in the closed mode, the expanding means having an expanded volume when in the open mode, the expanded volume being greater than the normal volume; and
    a moveable plug member located within the resilient member, the moveable plug member being longitudinally moveable as the valve transitions between the open and closed modes.

11. The valve as defined by claim 10 wherein the volume of the expanding means expands as the valve transitions from the closed mode to the open mode.

12. The valve as defined by claim 10 wherein the expanding means expands in response to receipt of a distally directed force.

13. The valve as defined by claim 12 wherein the expanding means has an inner dimension, the distally directed force causing the inner dimension of the expanding means to expand radially as the valve transitions toward the open mode.

14. The valve as defined by claim 10 further the plug member cooperates with the resilient member to form a flow controller that controls fluid flow through the valve, the flow controller being activated by a blunt tip.

15. The valve as defined by claim 10 wherein the expanding means has the normal volume when no radially compressive forces are applied to it.

16. The valve as defined by claim 10 wherein the expanding means is formed from a resilient material, the resilient material having a relaxed state when no more than a negligible force is applied to it, the expanding means having the normal volume when in the relaxed state.

17. A medical valve having a closed mode that prevents fluid flow, the medical valve also having an open mode that permits fluid flow, the medical valve comprising:
   an inlet;
   an outlet;
   a fluid channel between the inlet and the outlet; and
   a resilient member between the inlet and outlet, the resilient member forming a given portion of the fluid channel,
   the resilient member having a variable volume portion that forms the given portion of the fluid channel, the variable volume portion being in fluid communication with the outlet, the variable volume portion being defined by a resilient wall, the wall causing the variable volume portion to have a normal volume when in the closed mode, the wall causing the variable volume portion to have an enlarged volume when in the open mode, the enlarged volume being greater than the normal volume, the wall being forced radially outwardly from a relaxed state as the valve transitions from the closed mode toward the open mode; and
   a moveable plug member located within the resilient member, the moveable plug member being longitudinally moveable as the valve transitions between the open and closed modes.

18. The valve as defined by claim 17 wherein the wall is in the relaxed state when it receives no more than a negligible force.

19. The valve as defined by claim 17 wherein the volume of the variable volume portion expands as the valve transitions from the closed mode to the open mode.

20. The valve as defined by claim 17 wherein the wall is forced radially outwardly in response to receipt of a distally directed force.

21. The valve as defined by claim 20 wherein the variable volume portion of the resilient member has an inner dimension, the distally directed force causing the inner dimension of the variable volume portion to radially expand as the valve transitions toward the open mode.

22. The valve as defined by claim 17 wherein the resilient member includes a proximal portion located proximal of the variable volume portion, the proximal portion having a swabbable portion.

23. The valve as defined by claim 17 wherein the plug member cooperates with the resilient member to form a flow controller that controls fluid flow through the valve, the flow controller being activated by a blunt tip.

24. The valve as defined by claim 17 wherein the variable volume portion of the resilient member has the normal volume when no radially compressive forces are applied to it.

25. The valve as defined by claim 17 further comprising a housing that contains the resilient member, the housing having an inner surface spaced from the wall when in the closed mode, the wall and inner surface forming a space, the wall being free to expand into the space when the valve transitions toward the open mode.

26. A medical valve having a closed mode that prevents fluid flow, the medical valve also having an open mode that permits fluid flow, the medical valve comprising:
   a housing having an inlet and an outlet;
   a resilient member within the housing, the resilient member and housing forming a fluid channel between the inlet and the outlet, the fluid channel at least in part extending through the resilient member,
   the fluid channel having a given portion formed by a variable volume portion of the resilient member, the variable volume portion being in fluid communication with the outlet, the variable volume portion having a closed mode volume when in the closed mode, the variable volume portion being flexed to have an open mode volume when in the open mode, the open mode volume being greater than the closed mode volume; and
   a moveable plug located within the resilient member, the moveable plug member being longitudinally moveable as the valve transitions between the open and closed modes.

27. The medical valve as defined by claim 26 wherein the variable volume portion is flexed radially to have the open mode volume.

28. The medical valve as defined by claim 26 wherein the variable volume portion is in a normal state when in the closed mode.

29. The medical valve as defined by claim 26 further including a member that flexes the variable volume chamber as the valve transitions toward the open mode.

* * * * *